United States Patent [19]

Smikodub et al.

[11] Patent Number: 5,811,089
[45] Date of Patent: Sep. 22, 1998

[54] PHARMACEUTICAL PREPARATION BASED ON FETAL SUSPENSION AND METHODS OF TREATING ACQUIRED IMMUNE DEFICIENCY SYNDROME (HIV INJECTION)

[75] Inventors: Alexandr Ivanovich Smikodub; Igor Semenovich Markov; Elena Makarovna Pilipchak, all of Kiev, Ukraine

[73] Assignee: Centr Embrionainikh Tkaney "Emcell", Kiev, Ukraine

[21] Appl. No.: 505,236

[22] PCT Filed: Oct. 17, 1994

[86] PCT No.: PCT/UA94/00026

§ 371 Date: Aug. 9, 1995

§ 102(e) Date: Aug. 9, 1995

[87] PCT Pub. No.: WO95/16455

PCT Pub. Date: Jun. 22, 1995

[30] Foreign Application Priority Data

Dec. 14, 1993 [UA] Ukraine ................. 94061620

[51] Int. Cl.⁶ .................. C12N 5/08; A61K 38/00; A61K 39/00
[52] U.S. Cl. .................. 424/93.1; 424/93.21; 435/325
[58] Field of Search ............. 424/93.21; 435/240.2; 935/71

[56] References Cited

U.S. PATENT DOCUMENTS 3,937,816  2/1976  Jaeger et al. ................. 424/95
4,088,753  5/1978  Parmer ......................... 424/95
4,271,148  6/1981  Keeling ........................ 424/106

FOREIGN PATENT DOCUMENTS 0055487  7/1982  European Pat. Off. .
0537722  4/1993  European Pat. Off. .
9001326  2/1990  WIPO .

OTHER PUBLICATIONS

Touraine et al. "Fetal liver transplantation: Biology and clinical results," Bone Marrow Transplant, vol. 11:119–122, Nov. 1993.

Izzi et al. "Fetal Liver Transplant in A Plastic Anemia and Acute Leukemia", Fetal Liver Transplantation, 237–249 (1985).

Hassett et al., "Bone Marrow Transplantation in Aids", New England J. of Med., vol. 309, No. 1, p. 665 (1983).

Primary Examiner—Jasemine C. Chambers
Assistant Examiner—Karen M. Hauda
Attorney, Agent, or Firm—Abelman, Frayne & Schwab

[57] ABSTRACT

The invention relates, generally, to medicine, and particularly to cell therapy. Claimed is a medicinal preparation characterized by a certain composition and quantitative parameters of a cell suspension prepared from native or cryopreserved hemopoietic liver and/or spleen cells of a human embryo. Furthermore, claimed is a method of treating acquired immune deficiency syndrome (HIV infection) by administering the above medicinal preparation that is chosen from a tissue bank of various samples, taking into account individual indices of a patient, the same sample of preparation being used in repeated administration.

9 Claims, No Drawings

PHARMACEUTICAL PREPARATION BASED ON FETAL SUSPENSION AND METHODS OF TREATING ACQUIRED IMMUNE DEFICIENCY SYNDROME (HIV INJECTION)

FIELD OF THE INVENTION

This invention relates, generally, to medicine, and particularly to cell therapy, and can be applied for treating the acquired immune deficiency syndrome (HIV infection), as well as other diseases caused by occurrence of immune deficiencies.

BACKGROUND OF THE INVENTION

In recent years, a striking progress has taken place in the studies of human fetal cadaver tissues application. A completely new area of therapy is being developed, i.e. cell therapy that permits to fill an insufficient functional activity of damaged and sore tissues through the application of cell suspensions prepared from fetal tissues. Cell transplantation appears to be an attractive alternative for transplanting organs and tissues, since advantages of embryonic cells consist in the fact that they have not formed any strong individual characters of antigenic histocompatibility, are readily engrafted and do not induce the reaction of transplants against the host. In addition, cells feature a powerful vital potential. They proliferate, differentiate, and constitute a source of a vast number of biologically active substances.

At present, applied are cell suspensions prepared from fetal brain, bone marrow, liver, spleen, thymus, pancreas, and culocutaneous graft.

They are used for treatment of blood diseases such as primary and secondary myelodepressive states, immunity disorders, neural diseases, sugar diabetes etc.

The most successful initial attempts to apply cell suspensions as medicinal preparations involved human fetal liver.

In 1973, a medicinal preparation based on the cell suspension of native cells of a fetal liver of a 7-week gestation was prepared for the first time; administration of this preparation resulted in the recovery of hemopoiesis in a patient suffering from aplastic anemia (Kelemen E. Second J. Gematol., 1973, v. 10, No.4, pp.305–308).

In recent years, by varying methods of preparing cell suspensions and procedures of their application, research workers managed to achieve positive results of treating primary and secondary myelodepressive states (Lucarelli G., Izzi T., Porcelini A. Fetal liver transplantation. Alan R. Liss, 1985, pp.237–249).

A promising area of the clinical application of the above cell suspensions comprises immunity disorders, particularly in case of grave combined immune deficiency. Here, the most extensive clinical experience has been accumulated by Touraine J. L. (202 transplantations)—Transplantation Proceedings, 1993, v.25, No. 1, pp. 1067–1078.

At present, in the paper presented by Bacchetta R., Roncarolo M. J., Touraine J. L. Clin. Invest., 1993, v.91, March, pp.1067–1078) demonstrated are end results of treating two patients suffering from grave combined immune deficiency; here, not only immunity indices have been recovered in patients, but also presence of split chimerism and emergence of tolerance to both host and donor antigens have been demonstrated.

The authors of the present invention also have their own experience of using cell suspensions for treatment of immune disorders in cases of blood diseases.

The authors however do not have any information about application of these preparations for treatment of patients suffering from HIV infection (AIDS).

One of the most important mechanisms of HIV infection consists in a specific interaction between the HIV tunica albuginea (dr 120) and $CD_4$ protein expressed on the surface of immune cells pertaining to the $T_4$ lymphocytes class (helpers/inductors). The amount of cells carrying $CD_4$, $CD_8$, and $CD_{12}$ considerably decreases; $CD_4/CD_8$ ratio changes; a polyclonal stimulation of B lymphocytes and plasma cells is observed; activity of the mononuclear-macrophagal system reduces; amounts of NK and DN cells decreases.

In patients suffering from AIDS, hematologic disorders are observed, caused by the direct suppression of hemopoiesis by HIV infection, and resulting from medicamental effects, infiltrative processes of inflammatory, infectious or neoplastic nature. These disorders result in lymphopenia, leukopenia, anemia, and thrombocytopenia.

The most important fact however consists in the damage suffered by the immune system; the degree of such damage governs clinical forms of AIDS, terms of their progress, and the pattern of disease course.

Known in the art is treatment of patients having a developed clinical pattern of AIDS, with the use of transplantation of a cell suspension prepared from bone marrow (Hassett J. M., Zaroulis Ch.G., Greenberg M. L. et al. N.Engl. J. Med.; 1983, v.309, No.1, p.665).

This treatment method however features certain drawbacks.

Firstly, transplantation of cell suspensions based on bone marrow requires a thorough investigation into the tissue compatibility. Furthermore, donor and recipient have to undergo medicamental preparation; bacterial disinfection of intestine must be provided. Secondly, in spite of the identity of HLA and the above preparation, acute forms of cells functioning in the donor bone marrow are encountered in more than 50% of patients in the form of epidermal and hepatic necroses, hepatites, mycotic rejection by intestine mucous coat etc. Thirdly, the recovery of immunity has a selective and short-term nature (up to 4–6 weeks) and can be explained by the damage to bone marrow cells, caused by HIV infection. Clinical improvement is instable and considered to be questionable.

It is therefore the main object of the invention to develop such a medicinal preparation based on fetal cell suspension and having immune substituting effect, in which due to the optimal selection of cell composition indices it would be possible to intensify the mechanism of immune substitution and to attain positive results in the course of treatment of patients suffering from AIDS (HIV infection).

The object set forth is attained by that in a medicinal preparation having immune substituting effect and based on cell suspension prepared from native or cryopreserved hemopoietic liver and/or spleen cells of a human embryo of 5 to 12-weeks gestation, according to the invention, the contents of nucleated cells is 5 to $200 \cdot 10^6$/ml; the contents of colony-forming units of the granulomonocytic association, 20 to $200 \cdot 10^3$/ml; the contents of colony-forming units of granulocyte, erythrocyte, monocyte/macrophage, megakaryocyte 0.5 to $50 \cdot 10^3$/ml; and the contents of early precursors of hemopoiesis, 1 to $20 \cdot 10^6$/ml.

It has been empirically found that selection of the above indices of cell composition and quantitative ratio between the constituents permit to attain positive results of AIDS treatment.

The authors believe that such composition of the inventive medicinal preparation permits the most efficient filling of lacking cell and humoral factors of immunity by way of proliferation and differentiation of stem cells in HIV infected patients and those suffering from AIDS. Furthermore, the medicinal preparation of the invention, being a source of biologically active substances, causes a stimulating effect by activating cell and humoral mechanisms of recipient's immunity.

According to the present invention, it is expedient that in the course of cryopreservation, the medicinal preparation additionally contain dimethylsulfoxide in an amount of 3 to 10%. Selection of the lower limit is caused by the best shelf life of cells in the course of cryopreservation, while the upper limit value, by the toxic effect of the preparation.

The object set forth is also attained by that in a method of AIDS treatment, consisting in administration of a biologic material having immune substituting effect, according to the invention, the above biologic material having immune substituting effect is the inventive medicinal preparation.

The authors believe that medicinal preparations based on the above cell suspensions have been never used before for treatment of patients suffering from AIDS (HIV infection). The long-term research work on studying the mechanisms of effect of the preparations based on cell suspensions on the processes of treating various diseases however permits to state that the cell suspensions of the inventive composition can be successfully used for treatment of patients suffering from AIDS.

Application of cell suspensions based on hemopoietic and stem cells of human fetal hemopoietic organs is governed by the following mechanisms:

1. Under the effect of hemopoietic factors, stem cells are transformed to those hemopoiesis origins that are deficient in the human organism.

2. Central organs of immunogenesis in patients suffering from AIDS are damaged to a lesser extent than the peripheric link represented by T-lymphocytes. Therefore, embryonic-origin lymphocytes undergo "training" in the central organs of the immune system, that were not affected by any changes.

3. Patients suffering from AIDS demonstrate a substantial suppression of the delayed-action hypersensitivity reaction and up to complete anergy; therefore, a long-term effect of substitution without any correction with immunodepressants is possible.

4. Alongside with the correction of a hemoiesis lymphoid origin, there occurs the recovery of the myeloid origin, including megakaryocytic one, which fact is expressed by an increase in the amount of erythrocytes, leukocytes, and thrombocytes.

5. The matter of stability of hepomopoiesis fetal stem cells to HIV infection still remains open, though there exist some clinical data confirming this phenomenon.

6. Some promising results of combined treatment are available, when the preliminary etiotropic therapy reduces the probability of HIV-caused damage to fetal tissue as a result of interruption of the process of virus reproduction.

7. The method of treatment with human hemopoietic fetal liver and/or spleen cells and stem cells of hemopoiesis of human hemopoietic fetal organs is particularly recommended for patients who do not endure AZT and DDI.

The possibility of using cell suspensions prepared from hemopoietic cells and stem cells of hemopoiesis of human hemopoietic fetal organs is confirmed by clinical tests carried out by the authors. Observed in patients were considerable improvement of immune status indices and attainment of clinical and immunologic remission.

According to one aspect of the present invention, it is expedient to administer the inventive medicinal preparation in a dosage of 0.5 to 8 ml.

In addition, it is desirable to administer the above preparation prior to and/or after the therapy carried out with the use of etiotropic preparations.

It is expedient to choose the medicinal preparation from a tissue bank of various samples, taking into account individual indices of a patient; moreover, in cases of repeated administration, the same sample of preparation has to be used.

A fuller understanding of the nature of the invention will be had from the following detailed description of embodiments thereof, taken in conjunction with specific Examples.

DESCRIPTION OF PREFERRED EMBODIMENT

The medicinal preparation of the invention can be produced by using the following procedure:

Embryos are obtained after artificial abortions in healthy women who have been examined with respect to the absence of viral and hemic infections. Embryos from 5–8 weeks of age are used. Vacuum extraction method of abortion is preferrable to preserve the integrity of an embryo. The embryo is then transferred to a sterile vessel containing Hanks's solution and an antibiotic (group of aminoglycosides). Subsequent work is carried out under sterile conditions of a box.

Embryos are transferred to sterile Petri dishes filled with Hank's solution and antibiotic; here, after the abdominal cavity has been carefully opened, liver and spleen are extracted and used separately to prepare cell suspensions.

Hemopoietic organs are placed into homogenizers, cut into small fragments and ground to prepare a homogeneous mass. Cells are washed down, with Hank's solution, from homogenizer walls and pestle and into graduated test tubes, while passing them first through the filter used for transfusion of blood preparations, and then through diminishing diameter needles. A portion of the thus prepared suspension is transferred to a polyethylene container and closed hermetically. This portion will be used for the transplantation of the native cell suspension. The other portion will be subjected to cryopreservation.

Dimethylsulfoxide (DMSO, chemically pure) is used as a clyoprotector. Prior to its use, DMSO is passed through a millipore filter (pore diameter of 0.22 $\mu$m). With slight stirring, added in drops to the cell suspension is the equal volume of working solution of DMSO in an amount of 3 to 10%.

Cell suspensions are poured into 0.5 to 2 ml polyethylene containers (depending on further purposes). The containers are placed into the chamber of a programmable freezer using liquid nitrogen, and frozen to $-196°$ C.

Cryopreserved cell suspensions are stored in the bank of embryonic tissues at $-196°$ C.

After the cell suspension has been prepared, the following parameters are determined:

1st: amount of nucleated cells per 1 ml;

2nd: amount of colony-forming units of the granulomonocytic association (CFU GM) per 1 ml;

3rd: number of colony-formung blast units (CFU bl.) per 1 ml;

4th: amount of the early precursors of hemopoiesis ($CD_{34}$) per 1 ml.

Following this, the tissue bank is so shaped as to keep the parameters under investigation within the following limits:

1st: 5 to $200 \cdot 10^6$/ml

2nd: 20 to $200 \cdot 10^3$/ml

3rd: 0.5 to 50·10³/ml

4th: 1 to 20·10⁶/ml.

Prenatal diagnosis includes tests for syphilis, HIV infection, HBV and HCV, toxoplasmosis, cytomegaloviral infection. Contents of containers are tested for bacterial sterility.

Fetal diagnosis comprises tests for HIV infection, HBV and HCV, cytomegalovirus, viruses of rubella, herpes and toxoplasmosis.

Depending on a version of clinical treatment, the medicinal preparation is administered with the use of one of the following methods:

administration (transplantation) of a part of native hemopoietic cells, and subsequent administration of cryopreserved cells of a given sample, stored in the bank;

administration of the total native sample;

administration of a portion or the total cryopreserved material of a given sample.

Prior to, and in a number of cases after administration of the inventive medicinal preparation, etiotropic treatment of a patient has to be carried out, e.g. with azidothimidin in submaximum dosage till the occurrence of a clinical positive effect, improvement of immunologic indices, decrease of antibodies titer to HIV, and myelodepression phenomena.

The effect of treatment is evaluated from:

duration of clinical remission;

immunologic indices such as total amount of lymphocytes, contents of $CD_3$, $CD_4$, $CD_8$, and $CD_4/CD_8$ ratio;

amount of erythrocytes that contain fetal hemoglobin.

Detailed description of the use of the present invention in compliance with the clinical practice available with the authors is given in the following Examples.

EXAMPLE 1

Female patient 920034 "T", 37 years old, was admitted to the AIDS Department of the Kiev Research Institute for Epidemiology and Infectious Diseases on Feb. 23, 1993.

Diagnosis: clinical AIDS; pneumocystic pneumonia in the reconvalescence stage; chronic smoker's bronchitis; post-encephalitis state; candidiasis of intestine and respiratory tracts; chronic gastritis at the unstable remission stage; chronic cholecystitis at the unstable remission stage.

HIV infection was revealed in 1990; the patient was treated in Moscow till September, 1992. Her first stay with the AIDS Department of the Kiev Research Institute for Epidemiology and Infectious Diseases lasted from Sep. 17 till Oct. 26, 1992. The patient suffered from pneumocystic pneumonia.

On Oct. 23, 1992, the patient was transferred to resuscitation department with herpetic encephalitis; here, after the spinal puncture, spastic paraplegia and fallopian neuritis developed as a result of encephalitis.

The patient complained permanent headaches that were periodically aggravated, accompanied by nausea and sometimes by vomiting, as well as vertigo and periodic losses of consciousness. In addition, the patient suffered from cough accompanied by expectoration of small amounts of sputum, sensation of pain in bones ted to the AIDS Department with complaints of referred headache to light and left orand joints, weakness of muscles in lower extremities (walking while holding a support), facial asymmetry (right-side neumitis of the facial nerve). Body temperature periodically increased up to 39° C.

Objectively: intugements were pale and clean; small peripheric lymph nodes (up to 0.5 cm in diameter), movable, of elastic consistence, painless. Cardiac sounds were clear and rhythmic; respiration in lungs was rough, with diffused dry rale over the total surface.

The abdomen was soft and sensitive to palpation in the epigastric and right hypochondrium areas; stools and diuresis without any peculiarities.

The first transplantation of the cell suspension prepared from hemopoietic cells of human fetal liver was carried out on Mar. 4, 1993. The suspension was administered in an amount of 2.5 ml.

Parameters of the cell suspension were the following: sample 3037C-12H; embryo age, 9 weeks; amount of nucleated cells, 98·10⁶/ml; CFU GM, 26·10³/ml; CFU of granulocyte, erythrocyte, monocyte/macrophage, megakaryocyte 1.4·10³/ml; $CD_{34}$, 2.4·10⁶/ml. Method of administration was intravenous.

After transplantation, positive dynamics was observed, i.e. improvement of general state, emotional tonus and appetite. After several days, the cough decreased; it became easier for the patient to walk; the fever diminished. Rough respiration was still present in the lungs, however no rale was auscultated.

On Apr. 29, 1993, repeated transplantation was carried out (the same sample, in amount of 2.5 ml). The patient was discharged on Apr. 30, 1993 (for family reasons) in the satisfactory state.

The patient stayed once again at the AIDS Department from May 13 till Jul. 17, 1993. Headache, vertigo, pain in bones and joints were still present. Body temperature however did not increase; good appetite and sleep were observed; facial asymmetry diminished, cough disappeared; the patient could walk small distances without any support.

After her discharge on Jul. 7, 1993, the patient stayed at home in the city of Odessa where she endured herpes zoster of the hairy part of the head, accompanied by the body temperature increase and encephalopathy. Breakouts continued till Aug. 4, 1993.

TABLE 1

Dynamics of peripheral blood indices in female patient T.

| Date | Erythrocytes, $10^{12}/l$ | Hemoglobin, g/l | Color index | Leukocytes, $10^9/l$ | Basophils, % | Eosinophils, % | Related to slab neutrophile, % | Segmentnuclear, % | Lymphocytes, % | Monocytes, % | S.R., mm/hr |
|---|---|---|---|---|---|---|---|---|---|---|---|
| 25.03.93 | 4.0 | 129 | 0.9 | 8.8 | 1 | | 1 | 68 | 25 | 5 | 53 |
| 09.03.93 | 4.0 | 119 | 0.9 | 7.7 | | 3 | 1 | 40 | 42 | 5 | 60 |
| 18.03.93 | 4.0 | 119 | 0.9 | 8.9 | | | | | | | |
| 01.04.93 | 4.0 | 120 | 0.9 | 7.8 | 1 | 2 | 1 | 47 | 46 | 4 | 45 |

TABLE 1-continued

Dynamics of peripheric blood indices in female patient T.

| Date | Erythrocytes, $10^{12}/l$ | Hemoglobin, g/l | Color index | Leukocytes, $10^9/l$ | Basophils, % | Eosinophils, % | Related to slab neutrophile, % | Segmentnuclear, % | Lymphocytes, % | Monocytes, % | S.R., mm/hr |
|---|---|---|---|---|---|---|---|---|---|---|---|
| 13.04.93 | 4.0 | 128 | 0.9 | 7.6 | 1 | 3 | 1 | 40 | 50 | 6 | 33 |
| 18.05.93 | 4.0 | 132 | 0.9 | 8.9 |   | 2 | 2 | 40 | 46 | 2 | 45 |
| 01.06.93 | 2.9 | 100 |   | 6.4 | 1 | 1 | 1 | 50 | 43 | 4 | 38 |
| 08.07.93 | 3.8 | 115 |   | 4.0 | 1 | 2 | 3 | 66 | 25 | 3 | 40 |
| 01.08.93 |   |   |   | 6.2 | 1 | 3 | 4 | 67 | 23 | 2 | 21 |
| 21.09.93 | 4.1 | 130 | 0.9 | 3.5 |   | 2 | 1 | 44 | 50 | 3 | 59 |
| 07.10.93 |   |   |   | 4.4 | 1 |   | 1 | 64 | 26 | 5 | 58 |
| 02.11.93 | 4.1 | 129 | 0.9 | 3.8 | 1 | 2 | 2 | 60 | 30 | 5 | 44 |
| 11.11.93 | 4.0 | 130 | 0.9 | 3.9 | 2 | 2 | 1 | 60 | 31 | 4 | 60 |

TABLE 2

Dynamics of immune indices in female patient T.

| Date | CD3+ | CD4+ | CD8+ | HLADR | CD4/CD8 | SIg |
|---|---|---|---|---|---|---|
| 25.02.93 | 950 | 442 | 851 | 85 | 0.52 | 466 |
|  | 43.2 | 20.1 | 38.7 | 3.9 |  | 21.2 |
| 09.03.93 | 407 | 414 | 405 | 453 | 1.02 | 252 |
|  | 23.2 | 23.7 | 23.2 | 25.9 |  | 14.4 |
| 18.03.93 | 1807 | 1115 | 572 | 594 | 1.94 | 449 |
|  | 42.3 | 26.1 | 13.4 | 19.9 |  | 10.5 |
| 01.04.93 | 1690 | 793 | 377 | 384 | 2.1 | 459 |
|  | 47.1 | 22.1 | 10.5 | 10.7 |  | 12.8 |
| 13.04.93 | 1512 | 604 | 840 | 380 | 0.69 | 433 |
|  | 39.8 | 15.9 | 22.9 | 10.2 |  | 11.4 |
| 18.05.93 | 1641 | 528 | 810 | 394 | 0.65 | 438 |
|  | 40.1 | 12.9 | 19.8 | 8.9 |  | 10.7 |
| 01.06.93 | 1016 | 439 | 632 | 468 | 0.59 | 335 |
|  | 36.1 | 15.6 | 26.4 | 16.6 |  | 11.9 |
| 08.06.93 | 349 | 211 | 130 | 120 | 1.63 | 60 |
|  | 34.4 | 21.2 | 13.0 | 12.0 |  | 6.0 |
| 01.07.93 | 497 | 369 | 310 | 219 | 1.19 | 233 |
|  | 34.9 | 25.9 | 21.8 | 15.4 |  | 16.4 |
| 21.09.93 | 838 | 393 | 213 | 497 | 1.89 | 385 |
|  | 47.9 | 22.5 | 12.2 | 28.4 |  | 22.0 |
| 07.10.93 | 464 | 243 | 297 | 65 | 0.8 | 275 |
|  | 40.6 | 21.3 | 26.0 | 5.7 |  | 24.1 |
| 02.11.93 | 479 | 247 | 223 | 184 | 1.8 | 197 |
|  | 31.5 | 16.3 | 14.7 | 12.1 |  | 13.0 |
| 11.11.93 | 512 | 340 | 275 | 165 | 1.23 | 82 |
|  | 33.7 | 22.4 | 18.1 | 10.9 |  | 5.4 |

TABLE 3

Dynamics of biochemical indices in female patient T.

| Date | Bilirubin total | indirect | ALT | Thymol test | Total protein | Albumin | $\alpha 1$ | $\alpha 2$ | $\beta$ | $\gamma$ |
|---|---|---|---|---|---|---|---|---|---|---|
| 25.02.93 | 11.7 | 11.7 | 0.25 | 8.0 | 89.2 | 47.1 | 3.6 | 6.4 | 12.2 | 30.7 |
| 09.03.93 | 9.36 | 9.36 | 0.14 | 8.0 | 89.2 | 44.4 | 4.1 | 6.5 | 10.9 | 34.1 |
| 21.09.93 | 7.8 | 7.8 | 0.11 | 6.0 | 86.4 | 44.3 | 7.7 | 10.7 | 13.3 | 24.0 |
| 11.11.93 | 7.0 | 7.0 | 0.11 | 6.5 | 89.2 | 48.3 | 8.9 | 10.7 | 13.8 | 19.2 |

TABLE 4

Dynamics of analyses of the urine in female patient T.

| Date | Color | Transparency | Reaction | Density | Protein | Sugar | Leukocytes | Erythrocytes |
|---|---|---|---|---|---|---|---|---|
| 02.03.93 | Yellow | Transparent | Acidic | 1009 | — | — | 4–6 | 0–1 |
| 16.03.93 | Yellow | Transparent | Acidic | 1012 | — | — | 2–3 | 0–1 |
| 14.05.93 | Yellow | Transparent | Acidic | 1016 | 0.099 | — | 3–4 | 0–1 |
| 18.05.93 | Yellow | Transparent | Acidic | 1008 | 0.099 | — | 1–2 | 1–2 |

TABLE 4-continued

Dynamics of analyses of the urine in female patient T.

| Date | Color | Transparency | Reaction | Density | Protein | Sugar | Leuko-cytes | Erythro-cytes |
|---|---|---|---|---|---|---|---|---|
| 07.10.93 | Yellow | Transparent | Acidic | 1012 | — | — | 3–4 | 0–1 |
| 11.11.93 | Yellow | Transparent | Acidic | | 0.132 | — | Dense throughout all visual field | — |

TABLE 5

Immunofermental diagnostics in female patient T.

| Date | Ag p24 | Titer AT to p24 | AT env | AT cor | Titer of total AT to HIV | Titer AT to CMV | AT IgG to HSV | AT IgM to HSV | AT IgG to EBV | AT IgM to EBV |
|---|---|---|---|---|---|---|---|---|---|---|
| 08.11.93 | − | 1:3125 | + | + | 1:8000 | 1:800 | + | − | + | − |

TABLE 6

Immunoblotting in female patient T.

| Date | gp 160 | gp 120 | p 63 | p 55 | p 52 | gp 41 | p 34 | p 25 | p 18 |
|---|---|---|---|---|---|---|---|---|---|
| 09.02.94 | + | + | + | + | − | + | + | + | + |

On Sep. 9, 1993, the patient was admitbital cavities, aching pain and hindered movements in joints, increasing body temperature up to 37.3° to 38.2° C., aching epigastric pain, and cough accompanied by expectoration of thick of sputum having a purulent nature. Rough respiration was auscultated in the lungs together with dry rale on both sides (Oct. 19, 1993: pneumocysts in 48% of visual fields).

On Nov. 5, 1993, the third transplantation of the cell suspension of the same sample was carried out (1.5 ml). On Nov. 9, 1993, cough decrease was noted; body temperature was 37.2° C. No pneumocysts were revealed. The patient was discharged on Nov. 11, 1993 in the satisfactory state.

Tables 1 through 6 show the results of laboratory and immunologic tests.

At present, the state of the patient is satisfactory. Observation is being continued.

EXAMPLE 2

Male patient 930002 "V" was admitted to the AIDS Department of the Kiev Research Institute for Epidemiology and Infectious Diseases on Feb. 23, 1993.

Diagnosis: clinical AIDS; pneumocystic pneumonia in the reconvalescence stage; candidiasis of the oral cavity; chronic hepatitis transferring to cirrhosis; chronic iron deficiency anemia; chronic gastroduodenitis, moderate aggravation; esophagus diverticulum; relapsing internal hemorrhoids, aggravation stage.

Initial positive HIV reaction was revealed in 1992; the patient stayed with the AIDS Department from Dec. 29, 1992 till Feb. 11, 1993. During this period, he endured pneumocystic pneumonia.

Roentgenography of thorax organs, taken on Jan. 15, 1993: bronchovascular pattern is strengthened and fibrously changed, especially in lower lobes of lungs. Lung roots are heavy, coarse calcite being present in the right portion.

Conclusion: Chronic bronchitis. In the course of treatment, the patient received biceptol, nistatin, mucaltin, and polyvitamins. The patient was discharged in the satisfactory state.

During next admittance on Feb. 23, 1993, he complained weakness, fast fatiguability, poor appetite.

Objectively: intugements were pale. Peripheric lymph nodes: palpated are posterocervical, submandibular, cubital and inguinal ones (up to 1.0 cm in diameter), movable, painless, of elastic consistence.

Cardiac sounds were moderately weak and rhythmic; respiration in lungs was weakened, with rough shade. The abdomen was soft and painless. Liver edge was protruding from beyond the costal arch by 4 cm. The spleen was not palpated. No peripheric edemas were found.

On Mar. 4, 1993, the transplantation of the cell suspension prepared from hemopoietic cells of human fetal liver and spleen was carried out. Cell suspension parameters were the following: sample 3037C-37H; embryo age, 7 weeks; administered amount, 2.5 ml; amount of nucleated cells, $37 \cdot 10^6$/ml; CFU GM, $22 \cdot 10^3$/ml; CFU of granulocyte, erythrocyte, monocyte/macrophage, megakaryocyte $1.8 \cdot 10^3$/ml; $CD_{34}$, $3.4 \cdot 10^6$/ml. Method of administration was intravenous.

After transplantation, improvement of appetite and decrease of weakness were observed. In addition, decrease of hemoglobin and positive Gregersen's reaction were noted; however, surgeon's examination did not reveal any hemorrhage. According to the hematologist's prescription, the patient received tardiferon; patient's state was stable.

Tables 7 through 12 give the results of laboratory and immunologic tests.

The patient was discharged in the satisfactory state. Observation is still going on.

EXAMPLE 3

Male patient 910004 "N", 48 years old, was admitted to the AIDS Department of the Kiev Research Institute for Epidemiology and Infectious Diseases on May 24, 1993.

Diagnosis: clinical AIDS; pneumocystic pneumonia in the reconvalescence stage; onycomycosis; WPW syndrome.

Initial positive HIV reaction was revealed in 1991. In October, 1992, the patient endured pneumocystic pneumonia.

The patient was admitted for planned examination.

TABLE 7

Dynamics of peripheric blood indices in male patient V.

| Date | Erythrocytes, $10^{12}$/l | Hemoglobin, g/l | Color index | Leukocytes, $10^9$/l | Basophils, % | Eosinophils, % | Related to slab neutrophile, % | Segmentnuclear, % | Lymphocytes, % | Monocytes, % | S.R., mm/hr | Thrombocytes, $10^9$/l | |
|---|---|---|---|---|---|---|---|---|---|---|---|---|---|
| 25.02.93 | 4.5 | 146 | 0.9 | 5.9 | 1 | 1 | 1 | 47 | 44 | 6 | 45 | $310 \cdot 10^9$/l | |
| 30.03.93 | 3.6 | 76 | 0.8 | 9.5 | 0 | 1 | 2 | 51 | 43 | 3 | 78 | | anisocytosis+, hypochr.+, poikilocytosis+ |
| 05.03.93 | 3.5 | 68 | 0.8 | 8.9 | — | 2 | 2 | 70 | 23 | 3 | 68 | | hypochr.+ |
| 09.03.93 | 3.3 | 70 | 0.9 | 8.8 | — | 2 | 2 | 67 | 26 | 3 | 65 | | anisocytosis+, hypochr.+, poikilocytosis+ |
| 18.03.93 | 3.3 | 72 | 0.8 | 9.0 | — | 5 | 2 | 40 | 50 | 3 | 71 | $230 \cdot 10^9$/l | anisocytosis+ poikilocytosis+ |
| 23.03.93 | 3.1 | 72 | 0.8 | 8.7 | — | 2 | 2 | 45 | 46 | 5 | 48 | | |
| 30.03.93 | 3.3 | 74 | 0.8 | 6.4 | — | 2 | 2 | 51 | 42 | 3 | 65 | | |
| 06.04.93 | 3.4 | 75 | 0.8 | 8.7 | — | 2 | 2 | 46 | 46 | 4 | 61 | $160 \cdot 10^9$/l | |
| 13.04.93 | 3.5 | 79 | 0.8 | 8.4 | — | 2 | 1 | 41 | 53 | 3 | 60 | | hypochr.+ |

TABLE 8

Dynamics of analyses of the urine in male patient V.

| Date | Color | Reacction | Density | Transparency | Protein | Sugar | Leukocytes | Erythrocytes | Salts |
|---|---|---|---|---|---|---|---|---|---|
| 25.02.93 | Yellow | Acidic | 1015 | Transparent | 0.066 | — | 7–8 | 1–3 | Oxalates |
| 02.03.93 | Yellow | Acidic | 1007 | Transparent | None | — | 2–3 | | |
| 05.03.93 | Yellow | Acidic | 1021 | Transparent | 0.099 | — | 3–5 | 0–1 | |
| 15.03.93 | Yellow | Acidic | 1013 | Transparent | 0.033 | — | 1–3 | | |
| 29.03.93 | Yellow | Acidic | 1007 | Transparent | 0.033 | — | 4–5 | 0–1 | |

TABLE 9

Gregersen's reaction in male patient V.

| 09.03.93: positive | 19.03.93: sharply positive | 24.03.93: positive | 21.04.93: positive | 22.04.93: positive |
|---|---|---|---|---|

TABLE 10

Dynamics of immune indices in male patient V.

| Date | CD3+ | CD4+ | CD8+ | HLADR | CD4+/CD8+ | SIg |
|---|---|---|---|---|---|---|
| 25.02.93 | 859 | 631 | 566 | 41 | 1.11 | 260 |
| | 33.1 | 24.3 | 21.8 | 1.6 | | 10.0 |
| 09.03.93 | 796 | 821 | 637 | 212 | 1.29 | 1025 |
| | 19.5 | 20.1 | 15.6 | 5.2 | | 25.1 |
| 18.03.93 | 2200 | 1107 | 1048 | 337 | 1.06 | 450 |
| | 48.9 | 24.6 | 23.3 | 7.5 | | 10.0 |
| 30.03.93 | 454 | 382 | 269 | 148 | 1.42 | 261 |
| | 16.9 | 14.2 | 10.0 | 5.5 | | 9.7 |
| 13.04.93 | 913 | 839 | 690 | 436 | 1.25 | 313 |
| | 21.3 | 19.3 | 15.5 | 9.8 | | 8.4 |

TABLE 11

Dynamics of biochemical indices in male patient V.

| Date | Bilirubin total | di-rect | indi-rect | Thymol test | ALT | Total protein | Albumin | α1 | α2 | β | γ |
|---|---|---|---|---|---|---|---|---|---|---|---|
| 25.02.93 | 9.36 | — | 9.36 | 7.0 | 0.14 | 89.2 | 39.5 | 4.9 | 7.6 | 13.7 | 34.3 |
| 09.03.93 | 10.5 | — | 10.5 | 8.0 | 0.11 | 91.9 | 33.8 | 5.4 | 8.1 | 14.2 | 38.5 |

TABLE 12

Immunofermental diagnostics and immunoblotting in male patient V.

| Date | Titer AT | Date | gp 160 | gp 120 | gp 65 | p 55 | p 51 | p 41 | p 31 |
|---|---|---|---|---|---|---|---|---|---|
| 05.03. | 1:25600 | 05.03.93 | + | weak | + | + | + | + | weak |
| 10.03.93 | 1:12800 | | | | | | | | |
| 22.03.93 | 1:25600 | | | | | | | | |

The patient complained periodic increases of the body temperature up to subfebrile figures, pain in the lower parts of back. Roentgenography of thorax organs, taken on Jun. 2, 1993: lung fields without any visible pathology. Observed expansions of the shade of mediastinum along the right periphery in the area of taps of a superlobar bronchus and root of the lung are identified to be most probably caused by increase of lymph nodes.

On Jun. 3, 1993, the transplantation of the cell suspension prepared from hemopoietic cells of human fetal liver was carried out. Cell suspension parameters were the following: sample 3037C-24H; embryo age, 6 weeks; administered amount, 1.5 ml; amount of nucleated cells, $14 \cdot 10^6$/ml; CFU GM, $27 \cdot 10^3$/ml; CFU of granulocyte, erythrocyte, monocyte/macrophage, megakaryocyte $3.4 \cdot 10^3$/ml; $CD_{34}$, $3.4 \cdot 10^6$/ml.

After transplantation, improvement of the general state, temperature decrease and attenuation of pains in the back were observed.

On Jul. 1, 1993, the patient started medicinal starvation; during this period, weakness and sweating occurred. Since Jul. 15, 1993, steady subfebrile condition and infrequent morning cough with small amounts of sputum were noted.

On Jul. 23, 1993, pneumonia of the lower lobe of right lung was diagnosed. Cefasolin and biceptol were prescribed.

Since Aug. 6, 1993, the patient received gentamycin, biceptol, cefasolin, and mefenamic acid.

Roentgenography of thorax organs, taken on Aug. 20, 1993: pneumonic infiltration in the right lung has gone.

On Aug. 25, 1993, the patient was discharged in the satisfactory state.

Tables 7 through 12 give the results of laboratory and immunologic tests.

The patient is being periodically observed at the AIDS Department. No complaints are presented; the satisfactory state is maintained.

Observation is still going on.

EXAMPLE 4

Male patient 900007 "G" was admitted to the AIDS Department of the Kiev Research Institute for Epidemiology and Infectious Diseases on May 31, 1993.

Diagnosis: HIV infection, carrier; chronic smoker's bronchitis.

HIV infection was revealed in 1990, during patient's stay at a hospital for the reason of cholecystitis.

From May 17 till Jun. 7, 1993, the patient was treated at the AIDS department on occasion of the lacunar angina; since that time he has been on dispensary register and observed periodically.

On Jun. 3, 1993, the transplantation of the cell suspension prepared from hemopoietic cells of human fetal liver was carried out. Cell suspension parameters were the following: sample 3037-53H; embryo age, 8 weeks; administered amount, 3 ml, amount of nucleated cells, $78 \cdot 10^6$/ml; CFU GM, $44 \cdot 10^3$/ml; CFU of granulocyte, erythrocyte, monocyte/macrophage, megakaryocyte $2.4 \cdot 10^3$/ml; $CD_{34}$, $2.7 \cdot 10^6$/ml. Method of administration was intravenous.

The patient endured transplantation satisfactorily; no changes in his state were noted.

Since Jul. 23, 1993, the patient was treated at the AIDS Department on occasion of acute left lower-lobe pneumonia. (Roentgenography of thorax organs, taken on Jul. 23, 1993: infiltrative changes in the form of focal shades in the lower lobe of the left lung; the root is reactive; the right lung without any peculiarities). No pneumocystes were revealed in the course of sputum tests. General state demonstrated expressed weakness, sweating, and cough with expectoration of small amounts of sputum. For 20 days the patient received doxycyclin, biceptol, and nistatin; upon completion of the treatment course, he was discharged in the satisfactory state.

On Sep. 1, 1993, the repeated transplantation of cryopreserved cell suspension (the same sample) was carried out; the patient endured this transplantation satisfactorily. On Sep. 16, 1993, an increase in the body temperature of up to 37.7° C. was noted; it was accompanied by weakness, pains and aches throughout the body, and headache. On Sep. 17, 1993, the state normalized.

Tables 18 through 23 give the results of laboratory and immunologic tests.

On Sep. 24, 1993, the patient was discharged in the satisfactory state.

Up to now, his state is satisfactory.

EXAMPLE 5

Male patient 930024 "D" was admitted to the AIDS Department of the Kiev Research Institute for Epidemiology and Infectious Diseases on Aug. 27, 1993.

Diagnosis: clinical AIDS; generalized lymphodenopathy; oral cavity candidiasis; intestine lambliasis; enteritis of Proteus etiology; hypochromic anemia.

TABLE 13

Dynamics of peripheric blood indices in male patient N.

| Date | Erythrocytes, $10^{12}/l$ | Hemoglobin, g/l | Color index | Leukocytes, $10^9/l$ | Basophils, % | Eosinophils, % | Related to slab neutrophile, % | Segmentnuclear, % | Lymphocytes, % | Monocytes, % | S.R., mm/hr | Thrombocytes, $10^9/l$ |
|---|---|---|---|---|---|---|---|---|---|---|---|---|
| 25.05.93 | 4.2 | 132 | 0.9 | 5.2 | 1 | 2 | 1 | 46 | 45 | 5 | 7 | |
| 01.06.93 | 3.6 | 118 | | 5.0 | 1 | 2 | 1 | 47 | 46 | 3 | 4 | 135 |
| 08.06.93 | 3.6 | 120 | | 4.6 | 1 | 2 | 1 | 52 | 41 | 3 | 5 | 120 |
| 22.06.93 | 4.3 | 136 | 0.9 | 4.3 | | 2 | 2 | 54 | 40 | 2 | 6 | 160 |
| 01.07.93 | 4.3 | | | 8.0 | 2 | 1 | 2 | 56 | 35 | 4 | 5 | 150 |
| 08.07.93 | 4.3 | | | 6.7 | 1 | 2 | 1 | 46 | 47 | 3 | 7 | 200 |
| 15.07.93 | 4.2 | 138 | 0.9 | 6.9 | 1 | 3 | 1 | 52 | 38 | 1 | 7 | 234 |
| 28.07.93 | | | | 6.4 | | 2 | 1 | 55 | 37 | 5 | 10 | |
| 17.08.93 | 4.5 | 146 | 0.9 | 6.0 | 1 | 2 | 1 | 58 | 36 | 2 | 8 | |
| 01.02.94 | 4.3 | 133 | 0.9 | 4.9 | 1 | 2 | 2 | 53 | 38 | 4 | 5 | |

TABLE 14

Dynamics of immune indices in male patient V.

| Date | CD3+ | CD4+ | CD8+ | HLADR | CD4+/CD8+ | SIg |
|---|---|---|---|---|---|---|
| 25.05.93 | 31.9 | 21.8 | 14.1 | 13.0 | 1.55 | 12.0 |
| | 746 | 510 | 330 | 304 | | 281 |
| 01.06.93 | 40.2 | 15.6 | 13.5 | 6.0 | 1.15 | 11.2 |
| | 945 | 367 | 317 | 141 | | 213 |
| 08.06.93 | 34.3 | 22.2 | 14.2 | 11.7 | 1.56 | 5.1 |
| | 663 | 429 | 274 | 216 | | 98.5 |
| 17.06.93 | 41.1 | 23.3 | 19.5 | 14.7 | 1.19 | 19.6 |
| | 608 | 345 | 289 | 216 | | 290 |
| 22.06.93 | 33.9 | 26.3 | 24.3 | 22.2 | 1.08 | 29.1 |
| | 502 | 389 | 360 | 328 | | 43.1 |
| 01.07.93 | 34.7 | 25.0 | 20.5 | 15.3 | 1.22 | 15.1 |
| | 972 | 700 | 574 | 428 | | 423 |
| 08.07.93 | 21.0 | 8.8 | 19.1 | 30.8 | 0.46 | 18.7 |
| | 661 | 277 | 601 | 970 | | 589 |
| 15.07.93 | 41.7 | 21.5 | 24.0 | 10.3 | 0.89 | 7.2 |
| | 1093 | 564 | 629 | 240 | | 184 |
| 27.07.93 | 29.2 | 22.5 | 36.1 | 13.3 | 0.62 | 12.9 |
| | 691 | 533 | 855 | 315 | | 305 |
| 17.08.93 | 26.3 | 25.8 | 21.9 | 8.4 | 1.13 | 5.5 |
| | 584 | 573 | 486 | 126 | | 122 |

TABLE 15

Dynamics of biochemical indices in male patient N.

| Date | Bilirubin total | di-rect | Thymol test | ALT | Total protein | Albumin | α1 | α2 | β | γ |
|---|---|---|---|---|---|---|---|---|---|---|
| 25.05.93 | 8.17 | — | 3.5 | 0.14 | 72.4 | 67.0 | 3.0 | 5.4 | 10.0 | 19.6 |
| 29.06.93 | 9.36 | — | 3.5 | 0.29 | 83.5 | 52.0 | 4.6 | 7.7 | 13.9 | 21.8 |
| 08.07.93 | 18.72 | — | 7.0 | 0.11 | 78.0 | 60.9 | 3.5 | 6.0 | 9.6 | 20.0 |
| 19.07.93 | 10.53 | — | 3.5 | 0.11 | 72.4 | 49.8 | 5.7 | 8.5 | 13.5 | 22.5 |

TABLE 16

Immunofermental diagnostics in male patient N.

| Date | Ag p24 | Titer AT to p24 | AT env | AT cor | Titer of total AT to HIV | Titer AT to CMV | AT IgG to HSV | AT IgM to HSV | AT IgG to EBV | AT IgM to EBV |
|---|---|---|---|---|---|---|---|---|---|---|
| 14.07.93 | — | 1:3125 | + | + | 1:1600 | 1:800 | + | — | + | — |
| 25.07.93 | — | 1:3125 | + | + | 1:16000 | not studied | + | — | — | — |
| 23.08.93 | — | 1:3125 | ++ | ++ | 1:4000 | 1:800 | + | — | — | — |

TABLE 17

Immunoblotting in male patient N.

| Date | gp 160 | gp 120 | p 65 | p 55 | p 51 | gp 41 | p 31 | p 24 | p 18 |
|---|---|---|---|---|---|---|---|---|---|
| 05.03.93 | + | + | + | + | + | + | + | + | + |
|  | + | + | + | + | + | + | + | + | + |

The patient was revealed to be HIV infected in 1993, on occasion of a long-term (3 months) fever of up to 38° to 38.5° C., that could not be treated with the use of antibiotics (the patient was treating himself), and diarrhea of the same duration; all this caused HIV testing.

During admittance, the patient complained considerable weakness, sweating, body temperature increase of up to 39° C., headache, bad sleep, water stools 4 times a day. During the last several months the patient lost 10 kg of the body weight.

Objectively: intugements were pale. Peripheric lymph nodes: movable, painless, of elastic consistence; posterocervical—multiple, up to 0.5 cm in diameter; axillary—in groups of 3 to 5, up to 1 cm in diameter; inguinal, up to 0.5 cm.

Cardiac sounds were moderately weak and rhythmic; tachycardia. Respiration in lungs was vesicular, no rale auscultated. The abdomen was soft and painless. Liver edge was protruding from beyond the costal arch by 2 cm. No peripheric edemas were found.

Roentgenography of thorax organs, taken on Aug. 28, 1993: infiltrative changes in the upper lobe of left lung against the background of expressed bronchovascular pattern. The left root is expanded and structureless. Conclusion: pneumonia with localization in the upper lobe of left lung.

Examination by otolaryngologist: chronic subatrophic pharyngitis.

Treatment prescribed: cefasolin, biceptol, retrovir, metronidasol.

In spite of the therapy, the fever did not decrease; diarrhea continued; weakness increased; anemia progressed; lymph nodes got bigger.

Diagnosis: clinical AIDS; septic state.

On Sep. 12, 1993, the transplantation of the cell suspension prepared from hemopoietic cells of human fetal liver was carried out. Cell suspension parameters were the following: sample 3037-46H; embryo age, 10 weeks; administered amount, 4 ml; amount of nucleated cells, $110 \cdot 10^6$/ml; CFU GM, $39 \cdot 10^3$/ml; CFU of granulocyte, erythrocyte, monocyte/macrophage, megakaryocyte $2.0 \cdot 10^3$/ml; $CD_{34}$, $1.5 \cdot 10^6$/ml.

Method of administration: intraperitoneal.

After transplantation, the general state of the patient somewhat improved. The temperature decreased down to subfebrile values; intoxication phenomena, weakness and sweating diminished.

Table 24 through 29 show results of laboratory and immunologic tests.

By request of the patient, he was discharged. Pneumonia was gone during a month. At present, the patient's state is satisfactory, he continues taking retrovir.

TABLE 18

Dynamics of peripheric blood indices in male patient G.

| Date | Erythrocytes, $10^{12}$/l | Hemoglobin, g/l | Color index | Leukocytes, $10^9$/l | Basophils, % | Eosinophils, % | Related to slab neutrophile, % | Segment-nuclear, % | Lymphocytes, % | Monocytes, % | S.R., mm/hr |
|---|---|---|---|---|---|---|---|---|---|---|---|
| 01.06.93 | 4.7 | 155 | 0.9 | 3.9 | 1 | 1 | 1 | 59 | 37 | 2 | 7 |
| 08.06.93 | 4.8 | 155 |  | 4.7 | 1 | 2 | 1 | 51 | 42 | 3 | 8 |
| 10.06.93 | 4.5 | 158 | 0.9 | 5.0 | 1 | 3 | 1 | 50 | 42 | 4 | 12 |
| 17.06.93 | 4.2 | 136 | 0.9 | 4.4 |  | 2 | 2 | 51 | 38 | 6 | 13 |
| 08.07.93 | 4.6 |  |  | 5.5 |  | 2 | 1 | 50 | 43 | 4 | 8 |
| 27.07.93 |  |  |  | 5.7 |  | 2 | 1 | 36 | 53 | 8 | 17 |
| 05.08.93 |  |  |  | 3.9 |  | 3 | 1 | 46 | 49 | 1 | 15 |
| 02.09.93 | 5.2 | 155 | 0.9 | 7.8 | 1 | 2 | 1 | 31 | 64 | 1 | 6 |
| 14.09.93 | 5.0 | 151 | 0.9 | 8.3 |  | 10 | 3 | 52 | 33 | 2 | 17 |
| 16.09.93 | 5.1 | 150 | 0.9 | 8.0 |  | 8 | 1 | 50 | 38 | 3 | 18 |
| 21.09.93 | 5.0 | 150 | 0.9 | 5.8 |  | 2 | 2 | 59 | 33 | 4 | 6 |

TABLE 19

Dynamics of immune indices in male patient G.

| Date | CD3+ | CD4+ | CD8+ | HLADR | CD4+/CD8+ | SIg |
|---|---|---|---|---|---|---|
| 04.05.93 | 742 | 571 | 586 | 246 | 0.97 | 244 |
|  | 35.4 | 25.5 | 26.2 | 11.0 |  | 10.9 |
| 01.06.93 | 627 | 280 | 209 | 308 | 1.34 | 198 |
|  | 45.8 | 20.5 | 15.3 | 22.5 |  | 14.5 |
| 08.06.93 | 670 | 448 | 238 | 103 | 1.84 | 115 |
|  | 33.2 | 22.2 | 11.8 | 5.3 |  | 5.7 |
| 10.06.93 | 651 | 485 | 256 | 218 | 1.84 | 105 |
|  | 31.0 | 23.1 | 12.2 | 10.4 |  | 5.0 |
| 17.06.93 | 543 | 456 | 238 | 226 | 1.9 | 318 |
|  | 31.7 | 26.6 | 13.9 | 13.2 |  | 21.3 |
| 08.07.93 | 868 | 348 | 319 | 726 | 1.08 | 610 |
|  | 36.7 | 14.7 | 13.5 | 30.8 |  | 25.8 |
| 27.07.93 | 634 | 797 | 838 | 326 | 0.94 | 519.6 |
|  | 21.0 | 26.4 | 27.8 | 10.8 |  | 17.2 |

TABLE 19-continued

Dynamics of immune indices in male patient G.

| Date | CD3+ | CD4+ | CD8+ | HLADR | CD4+/CD8+ | SIg |
|---|---|---|---|---|---|---|
| 05.08.93 | 585 | 420 | 155 | 483.5 | 2.77 | 189 |
|  | 30.6 | 22.0 | 8.1 | 25.3 |  | 9.9 |
| 02.09.93 | 1870 | 1227 | 1110 | 613.5 | 1.01 | 1065 |
|  | 65 | 24.2 | 21.0 | 21.1 |  | 21.8 |
| 14.09.93 | 972 | 789 | 597 | 446 | 1.32 | 828 |
|  | 35.5 | 28.8 | 21.8 | 16.3 |  | 30.2 |
| 16.09.93 | 976 | 623 | 690 | 748 | 0.9 | 472 |
|  | 32.1 | 20.5 | 22.7 | 24.6 |  | 15.8 |
| 21.09.93 | 523 | 275 | 599 | 530 | 0.46 | 281 |
|  | 27.3 | 14.4 | 31.3 | 27.7 |  | 14.7 |

TABLE 20

Dynamics of biochemical indices in male patient G.

| Date | Bilirubin total | indirect | ALT | Thymol test | Total protein | Albumin | α1 | α2 | β | γ |
|---|---|---|---|---|---|---|---|---|---|---|
| 07.06.93 | 7.0 | 7.0 | 0.14 | 8.0 | 86.4 | 50.9 | 7.2 | 8.4 | 12.5 | 21.0 |
| 08.07.93 | 18.72 | 18.72 | 0.11 | 5.5 |  |  |  |  |  |  |
| 27.07.93 | 9.36 | 9.36 | 0.42 | 2.0 | 80.8 | 53.5 | 7.0 | 8.0 | 9.5 | 22.0 |
| 02.09.93 | 12.0 | 12.0 | 0.2 | 1.5 | 72.4 | 59 | 4.0 | 9.0 | 10.0 | 18.0 |
| 14.09.93 | 3.0 | 3.0 | 0.11 | 3.5 |  |  |  |  |  |  |

TABLE 21

Dynamics of analyses of the urine in male patient G.

| Date | Color | Transparency | Reaction | Density | Protein | Sugar | Leukocytes | Erythrocytes |
|---|---|---|---|---|---|---|---|---|
| 02.06.93 | L/yellow | Transparent | Acidic | 1016 | Traces | — | 3–4 | 0–1 |
| 17.06.93 | L/yellow | Transparent | Acidic | 1021 | — | — | 3 | — |
| 08.07.93 | Yellow | Transparent | Acidic | 1014 | — | — | 5–6 | 0–1 |
| 03.09.93 | Yellow | Transparent | Acidic | 1013 | — | — | 0–1 | — |
| 15.09.93 | Yellow | Transparent | Acidic | 1013 | 0.033 | — | 4–5 | 0–1 |

TABLE 22

Immunofermental diagnostics in male patient G.

| Date | Ag p24 | Titer AT to p24 | AT env | AT cor | Titer of total AT to HIV | Titer AT to CMV | AT IgG to HSV | AT IgM to HSV | AT IgG to EBV | AT IgM to EBV |
|---|---|---|---|---|---|---|---|---|---|---|
| 23.09.93 | − | 1:2921.5 | + | + | 1:6400 | 1:800 | 1:200 | − | + | − |
| 26.10.93 | − | 1:2771.3 | + | + | 1:8000 | not studied | + | − | + | − |

TABLE 23

Immunoblotting in male patient G.

| Date | gp 160 | gp 120 | p 65 | p 55 | p 51 | gp 41 | p 31 | p 24 | p 18 |
|---|---|---|---|---|---|---|---|---|---|
| 27.10.93 | + | + | + | + | + | + | + | + | + |

EXAMPLE 6

Female patient 91005 "N", 25 years old, was admitted to the AIDS Department of the Kiev Research Institute for Epidemiology and Infectious Diseases on Apr. 21, 1993.

Diagnosis: clinical AIDS; pneumocystic pneumonia in the reconvalescence stage; candidiasis of oral and bronchi mucous membranes; allergic blepharoconjunctivitis; chronic hepatitis with transfer to cirrhosis; portal hypertensin; ascites; hepatolienal sybdrome.

HIV infection was diagnosed in 1989; the patient was treated in Moscow, received azidotimidin.

Since Dec. 15, 1991, the patient has been under observation at the AIDS Department.

From Nov. 11 till Dec. 22, 1992, she was treated at the AIDS Department with the following diagnosis: AIDS; pneumocystic pneumonia. From Nov. 24 till Dec. 22, 1992, asidotimidin therapy was applied with the daily dosage of 1000 mg; during patient's discharge from the hospital, she was recommended to keep on taking 500 mg/day for two weeks.

From Jan. 31 till Mar. 16, 1993, the patient was treated at the AIDS Department. She was taking retrovir from Feb. 18, 1993 till Mar. 16, 1993, in a daily dosage of 500 mg, and was discharged with recommendations to keep on taking retrovir in a daily dosage of 500 mg for several weeks. During the period of retrovir therapy, her general state improved (cough diminished, body weight increased by 4 to 5 kg); cell immunity parameters also improved.

During her admittance on Apr. 21, 1993, the patient complained weakness, dry cough, aching pain in the right hypochondrium, periodic nasal bleeding, tongue burning, undue fatiguability, throat pain in swallowing, eye burning.

Objectively: relatively satisfactory general state; intugements without any peculiarities. Palpated peripheric lymph nodes: submandibular and posterocervical: in the shape of chains of up to 0.5 cm in diameter; axillary, in groups of 3 to 5 and 0.7 to 1.0 cm in diameter; all the nodes were of elastic consistence, mobile and painless.

TABLE 27

Dynamics of immune indices in male patient D.

| Date | CD3+ | CD4+ | CD8+ | HLADR | CD4+/CD8+ | SIg |
|---|---|---|---|---|---|---|
| 31.08.93 | 421 | 282 | 399 | 323 | 0.66 | 429 |
|  | 36.9 | 24.7 | 35 | 28.3 |  | 37.6 |
| 09.09.93 | 491 | 221 | 353 | 260 | 0.63 | 309 |
|  | 37.0 | 16.7 | 26.6 | 19.6 |  | 23.3 |
| 21.09.93 | 464 | 431 | 431 | 297 | 1.0 | 479 |
|  | 22.5 | 20.9 | 20.9 | 14.4 |  | 23.2 |
| 27.09.93 | 283 | 93.5 | 93.5 | 697 | 2.28 | 120 |
|  | 30.0 | 9.9 | 9.9 | 7.8 |  | 12.7 |
| 07.10.93 | 299 | 310 | 310 | 199 | 0.6 | 343 |
|  | 31.6 | 32.8 | 32.8 | 21.1 |  | 36.3 |

TABLE 24

Dynamics of peripheric blood indices in male patient D.

| Date | Erythrocytes, $10^{12}/l$ | Hemoglobin, g/l | Color index | Leukocytes, $10^9/l$ | Basophils, % | Eosinophils, % | Related to slab neutrophile, % | Segment-nuclear, % | Lymphocytes, % | Monocytes, % | S.R., mm/hr | Thrombocytes, $10^9/l$ |
|---|---|---|---|---|---|---|---|---|---|---|---|---|
| 31.08.93 | 3.5 | 97 |  | 6.0 | 1 | 3 | 4 | 72 | 19 | 1 | 35 |  |
| 02.09.93 | 3.4 | 95 | 0.9 | 9.8 | 1 | 3 | 3 | 72 | 18 | 3 | 45 | 347 |
| 09.09.93 | 3.4 | 98 | 0.8 | 10.2 |  | 3 | 4 | 76 | 13 | 4 | 65 |  |
| 10.09.93 | 3.5 | 95 | 0.8 | 9.6 |  |  |  |  |  |  | 48 | 280 |
| 21.09.93 | 4.4 | 110 | 0.8 | 8.6 | — | 2 | 1 | 67 | 24 | 6 | 30 |  |
| 28.09:93 | 4.7 | 120 | 0.8 | 8.3 | — | 2 | 1 | 67 | 27 | 4 | 30 |  |
| 30.09.93 | 4.5 | 110 | 0.8 | 8.7 | — | 2 | 2 | 71 | 20 | 5 | 60 |  |

TABLE 25

Dynamics of biochemical indices in male patient D.

| Date | Bilirubin total | indirect | Thymol test | ALT | Total protein | Albumin | α1 | α2 | β | γ |
|---|---|---|---|---|---|---|---|---|---|---|
| 31.08.93 | 9.3 | — | 1.0 | 0.11 | 69.6 | 41 | 7 | 12 | 18 | 22 |
| 02.09.93 | 5.6 | — | 1.0 | 0.22 | 72.4 | 44 | 8 | 10 | 18 | 20 |
| 09.09.93 | 19.9 | 10.2 | 0.5 | 0.22 | 72.4 | 30 | 11 | 13 | 15 | 31 |
| 23.09.93 | 3.8 | — | 1.5 | 0.39 | 69.6 | 44 | 8 | 10 | 17 | 21 |
| 30.09.93 | 7.0 | — | 1.0 | 0.39 | 66.9 | 35.3 | 7.8 | 9.4 | 16.0 | 31.5 |

TABLE 26

Dynamics of analyses of the urine in male patient D.

| Date | Color | Reaction | Density | Transparency | Protein | Sugar | Leukocytes | Erythrocytes | Cylinders hyal. | gran. | Salts |
|---|---|---|---|---|---|---|---|---|---|---|---|
| 30.08.93 | saturated | Acidic | 1015 | Turbid | 0.66 | — | 3-5 | 0-1 | 0-1 | 0-1 | oxalate |
| 07.09.93 | L/yellow | Acidic | 1015 | Transparent | 0.33 | — | 1-3 | — | 0-1 |  |  |
| 09.09.93 | L/yellow | Acidic | 1014 | Turbid | 0.165 | — | 2-3 | 0-1 | 0-1 | 0-1 |  |
| 14.09.93 | L/yellow | Acidic | 1008 | Transparent | 0.33 | — | 5-6 | — | 2-3 | 1-2 |  |
| 30.09.93 | L/yellow | Acidic | 1020 | Transparent | 0.165 | — | 8-10 | 0-1 | 1-2 |  |  |

TABLE 28

Immunofermental diagnostics in male patient D.

| Date | Titer AT |
|---|---|
| 02.09.93 | 1:102400 |
| 22.09.93 | 1:6400 |

TABLE 29

Immunoblotting in male patient D.

| Date | gp 160 | gp 120 | p 65 | p 55 | p 53 | gp 41 | p 31 | p 25 | p 18 |
|---|---|---|---|---|---|---|---|---|---|
| 01.09.93 | + | + | + | − | weak | + | + | + | + |

Cardiac sounds were moderately weak and rhythmic with systolic murmur at the apex. Respiration in lungs was vesicular. The abdomen was soft and sensitive in the right hypochondrium, its volume being somewhat increased because of ascites. Liver edge was protruding from beyond the costal arch by 5 cm. A big and dense spleen was palpated.

On May 3, 1993, transplantation of the cell suspension prepared from hemopoietic cells of human fetal liver was carried out. The patient endured this transplantation satisfactorily. Parameters of the cell suspension were the following: sample 3037-81H; embryo age, 7 weeks; amount administered, 2 ml; amount of nucleated cells, $28 \cdot 10^6$/ml; CFU GM, $23 \cdot 10^3$/ml; CFU bl., $2.4 \cdot 10^3$/ml; $CD_{34}$, $1.8 \cdot 10^6$/ml. Method of administration was intravenous.

After transplantation, improvement of appetite was noted; the patient felt better.

On May 26, 1993, the patient was discharged in the satisfactory state; she categorically refused to take retrovir any more.

Tables 30 through 35 give the results of laboratory and immunologic tests.

Observation is still going on.

EXAMPLE 7

Male patient 930009 "V", 41 years old, was admitted to the AIDS Department of the Kiev Research Institute for Epidemiology and Infectious Diseases on Mar. 24, 1993.

Diagnosis: clinical AIDS; disseminated pulmpnary tuberculosis; candidiasis of the oral cavity and intestine.

HIV infection was revealed in March, 1993. Since the end of December, 1992, the patient feels general weakness, headache, temperature increase of up to 37.3° to 38° C., pain in the joints of lower extremities and crus muscles, aches and pains in all the bones and joints, chilling.

For the first time he saw a physician on Feb. 2, 1993; the diagnosis was polyarthritis.

On Feb. 2, 1993, the patient was consulted by a hematologist: attention should be drawn to increased liver and spleen. The patient has to be examined for chronic hepatitis and manifestations of hypersplenism (Hb, 96 g/l; thromb., 124000).

TABLE 30

Dynamics of peripheric blood indices in female patient N.

| Date | Erythrocytes, $10^{12}$/l | Hemoglobin, g/l | Color index | Leukocytes, $10^9$/l | Basophils, % | Eosinophils, % | Related to slab neutrophile, % | Segment-nuclear, % | Lymphocytes, % | Monocytes, % | S.R., mm/hr |
|---|---|---|---|---|---|---|---|---|---|---|---|
| 16.11.92 | 4.0 | 124 | 0.9 | 5.6 | 1 | 2 | 1 | 49 | 50 | 4 | 42 |
| 09.12.92 | 3.8 | 114 | 0.9 | 6.0 | | 1 | 1 | 26 | 68 | 4 | 60 reticulocytes: 10%; thrombocytes, $220 \cdot 10^9$/l |
| 02.02.93 | 3.9 | 127 | 0.9 | 8.9 | | 1 | 1 | 33 | 61 | 4 | 53 |
| 05.03.93 | 3.9 | 128 | 0.9 | 4.7 | | 2 | 1 | 45 | 48 | 4 | 45 |
| 12.04.93 | 4.0 | 121 | 0.9 | 7.6 | | 1 | 1 | 40 | 53 | 5 | 47 |
| 10.05.93 | 4.0 | 126 | 0.9 | 4.0 | | 2 | 1 | 46 | 49 | 2 | 45 |
| 24.05.93 | 4.1 | 133 | 0.9 | 4.0 | | 2 | 2 | 40 | 53 | 3 | 48 |

TABLE 31

Dynamics of immune indices in female patient N.

| Date | CD3+ | CD4+ | CD8+ | HLADR | CD4+/CD8+ | SIg |
|---|---|---|---|---|---|---|
| 18.11.92 | 21.3 | 14.4 | 22.0 | 26.4 | 0.65 | 4.7 |
| | 596 | 403 | 616 | 7393 | | 132 |
| 09.12.92 | 27.3 | 15.7 | 12.0 | 7.5 | 1.3 | 8.7 |
| | 1114 | 640 | 490 | 306 | | 355 |
| 01.02.93 | 48.3 | 13.3 | 56.0 | 9.5 | 0.2 | 6.8 |
| | 2623 | 722 | 2257 | 383 | | 369 |
| 01.03.93 | 75.2 | 10.9 | 66.0 | 6.1 | 0.17 | 5.4 |
| | 1697 | 246 | 1489 | 138 | | 122 |
| 12.04.93 | 56.0 | 13.4 | 42.7 | 11.1 | 0.31 | 11.4 |
| | 2240 | 539 | 1708 | 444 | | 456 |
| 10.05.93 | 56.5 | 5.5 | 35.0 | 35.2 | 0.16 | 2.5 |
| | 1107 | 108 | 686 | 690 | | 49 |
| 24.05.93 | 66.5 | 8.3 | 56.2 | 39.7 | 0.15 | 2.6 |
| | 1410 | 176 | 1191 | 842 | | 55 |

TABLE 32

Dynamics of biochemical indices in female patient N.

| Date | Bilirubin total | direct | Thymol test | ALT | Total protein | Albumin | α1 | α2 | β | γ |
|---|---|---|---|---|---|---|---|---|---|---|
| 12.04.93 | 4.68 | — | 12.0 | 0.79 | 86.4 | 34.1 | 4.2 | 6.4 | 12.4 | 42.9 |
| 24.05.93 | 18.72 | — | 9.5 | 0.71 | 94.8 | 40.6 | 5.1 | 6.3 | 13.9 | 34.1 |

TABLE 33

Dynamics of analyses of the urine in female patient N.

| Date | Color | Reaction | Density | Protein | Leukocytes | Erythrocytes |
|---|---|---|---|---|---|---|
| 11.04.93 | Yellow | Acidic | 1022 | 0.099 | 4-5 | 0-1 |
| 18.05.93 | Yellow | Acidic | 1020 | None | 3-5 | 0-1 |
| 23.05.93 | Yellow | Acidic | 1016 | 0.033 | 1-0 | 0-1 |

TABLE 34

Immunofermental diagnostics in female patient N.

| Date | Titer AT to Ag p 24 | Titer AT to p 24 | AT env | AT cor | Titer of total AT to HIV | Titer AT to CMV | AT IgG to HSV | AT IgM to HSV | AT IgG to EBV | AT IgM to BBV |
|---|---|---|---|---|---|---|---|---|---|---|
| 16.11.92 | + | 1:5 | + | + | 1:12800 | 1:320 | + | neg. | + | not studied |
| | % of vironeutral AT versus Ag p 24: 78% | | | | | | | | | |
| 01.02.93 | − | 1:8.1 | + | + | 1:32000 | 1:1600 | + | neg. | + | − |
| | % of vironeutral AT versus Ag p 24: 78% | | | | | | | | | |
| 12.04.93 | − | 1:5.0 | + | + | 1:16000 | 1:800 | + | − | + | − |

TABLE 35

Immunoblotting in female patient N.

| Date | gp 160 | gp 120 | p 68 | p 55 | p 52 | gp 41 | p 34 | p 25 | p 18 |
|---|---|---|---|---|---|---|---|---|---|
| 17.11.92 | + | + | + | + | + | + | + | + | + |
| 14.04.93 | + | + | + | + | + | + | + | + | |

The patient was taking ascorbic acid; folic acid; vitamins B1, B6, and B12; nicotinic acid; splenin, analgin, indometacin.

Blood count, Mar. 2, 1993: Hb, 105 g/l; Er, $3.8 \cdot 10^{12}/l$; CI, 0.9; thrombocytes, $135 \cdot 10^9/A$; S.R., 5 mm/hr.

Since Mar. 4, 1993, the patient was taking prednisolon. After the beginning of this treatment course, he noted improving state (decrease of pain and the feeling of tied-down joints). Since Mar. 28, 1993, the patient was taking retrovir, and since Apr. 6, 1993, biceptol (intravenously).

Roentgenography of thorax organs, taken on April 7, 1993: multiple focal shades of infiltrative nature over the total length of lungs, against the background of pneumosclerosis; expanded roots.

Conclusion: microfocal pneumonia has to be differentiated from the focal tuberculosis of the lungs.

After the consultation provided by a phthisiologist, antituberculosis threpy was prescribed, i.e. rifampicin, etambutol, isoniasid, streptomicin. On Apr. 21, 1993, the body temperature decreased and was subsequently within 36.4° to 36.8° C.

This temperature decrease was accompanied by the general state improvement, i.e. disappearance of dyspnea, decrease of cough and weakness. At the same time, aching pain in joints, hands in particular, periodic nausea, headache, vertigo, and quick fatiguability still remained.

On Jul. 15, 1993, the transplantation of the cell suspension prepared from hemopoietic cells of human fetal liver was carried out. Cell suspension parameters were the following: sample 3037-19H; embryo age, 10 weeks; administered amount, 4 ml; amount of nucleated cells, $142 \cdot 10^6$/ml; CFU GM, $64 \cdot 10^3$/ml; CFU of granulocyte, erythrocyte, monocyte/macrophage, megakaryocyte $1.3 \cdot 10^3$/ml; $CD_{34}$, $1.8 \cdot 10^6$/ml.

Method of administration: intraosseous.

The patient endured transplantation satisfactorily, though the next morning the body temperature increased up to 37.2° C. By the same evening, the temperature normalized. In the morning of Jul. 20, 1993, the body temperature increased up to 38° C., cutis hyperemia of forearms and lower extremities, accompanied by itch, appeared (total blood count: 9% eosinophils). On the next day after taking diasolin, the state normalized.

On Jul. 27, 1997, the patient noted satisfactory state for the first time since his admittance to the hospital. Headache, nausea and fatiguability decreased; pain in joints and right hypochondrium disappeared; appetite improved; the patient was able to perform physical work.

Satisfactory state lasted one week. On Aug. 6, 1993, slight cutis hyperemia of chest, upper and lower extremities appeared, accompanied by itch and temperature increase up to 38° C. This temperature remained for two days, although it was not accompanied by any significant change of state.

After several days, the state normalized.

On Sep. 10, 1993, the patient was discharged in the satisfactory state and with recommendations to continue antituberculosis therapy.

Tables 36 through 41 give results of laboratory and immunologic tests.

Observation is still going on.

Thus, the inventive medicinal preparation and method of treatment of acquired immune deficiency syndrome (HIV infection) with the use of said preparation permit:

to attain the clinical remission of disease;

to improve immunologic parameters;

to restore hemopoiesis;

to reduce intoxication.

The inventive medicinal preparation based on cell suspension may be used both independently, particularly in cases of intolerance and presence of contraindications for application of eryothropic therapy, and in combined treatment procedures.

In addition, cell suspensions of the inventive composition may be stored in pharmacies/banks of cryopreserved tissues and, taking into account lack of the need to identify histocompatibility antigenes, provide (in case of availability of relevant indications) a simpler application than e.g. blood transfuision.

TABLE 36

Dynamics of peripheric blood indices in male patient V.

| Date | Erythrocytes, $10^{12}/l$ | Hemoglobin, g/l | Color index | Leukocytes, $10^9/l$ | Basophils, % | Eosinophils, % | Related to slab neutrophile, % | Segmentnuclear, % | Lymphocytes, % | Monocytes, % | S.R., mm/hr | Thrombocytes |
|---|---|---|---|---|---|---|---|---|---|---|---|---|
| 15.03.93 | 4.4 | 139 | 0.9 | 4.5 | 1 | 1 | 2 | 58 | 34 | 4 | 14 | |
| 24.03.93 | 4.4 | 138 | 0.9 | 5.2 | | 2 | 1 | 56 | 36 | 5 | 13 | |
| 12.04.93 | 4.2 | 132 | 0.9 | 6.0 | 1 | 2 | 1 | 56 | 38 | 2 | 46 | $240 \cdot 10^9/l$ |
| 18.04.93 | 4.1 | 131 | 0.9 | 8.6 | | | 1 | | | | 60 | |
| 26.04.93 | 4.2 | 129 | 0.9 | 3.9 | 1 | 1 | 1 | 43 | 50 | 4 | 60 | |
| 17.05.93 | 4.3 | 133 | 0.9 | 4.1 | | 2 | 1 | 44 | 49 | 4 | 38 | |
| 02.06.93 | 4.1 | 132 | 0.9 | 4.0 | 1 | 2 | 1 | 34 | 58 | 4 | 50 | |
| 26.06.93 | 4.3 | 132 | 0.9 | 2.1 | | 2 | 2 | 36 | 56 | 4 | 25 | |
| 04.07.93 | 3.7 | 108 | 0.9 | 1.9 | | | | | | | 18 | $160 \cdot 10^9/l$ |
| 07.07.93 | 3.7 | 112 | 0.9 | 2.4 | | | | | | | 27 | |
| 14.07.93 | 3.7 | 110 | 1.0 | 2.5 | 1 | 2 | 2 | 13 | 78 | 4 | 40 | |
| 21.07.93 | 4.0 | 96 | 0.7 | 3.2 | 1 | 9 | 1 | 40 | 46 | 4 | 40 | |
| 02.08.93 | 3.8 | 108 | 0.8 | 2.5 | | 5 | 1 | 43 | 41 | 9 | 23 | |
| 09.08.93 | 4.0 | 124 | 0.9 | 3.7 | | 13 | 1 | 42 | 41 | 3 | 45 | |

TABLE 37

Dynamics of immune indices in male patient V.

| Date | CD3+ | CD4+ | CD8+ | HLADR | CD4+/CD8+ | SIg |
|---|---|---|---|---|---|---|
| 15.03.93 | 21.3 | 14.4 | 22.0 | 26.4 | 0.65 | 4.7 |
| | 596 | 403 | 616 | 7393 | | 132 |
| 12.04.93 | 27.3 | 15.7 | 12.0 | 7.5 | 1.3 | 8.7 |
| | 1114 | 640 | 490 | 306 | | 355 |
| 17.05.93 | 48.3 | 13.3 | 56.0 | 9.5 | 0.2 | 6.8 |
| | 2623 | 722 | 2257 | 383 | | 369 |
| 14.07.93 | 75.2 | 10.9 | 66.0 | 6.1 | 0.17 | 5.4 |
| | 1697 | 246 | 1489 | 138 | | 122 |
| 28.07.93 | 56.0 | 13.4 | 42.7 | 11.1 | 0.31 | 11.4 |
| | 2240 | 539 | 1708 | 444 | | 456 |

TABLE 38

Dynamics of biochemical indices in male patient V.

| Date | Bilirubin total | direct | indirect | Thymol test | ALT | Total protein | Albumin | α1 | α2 | β | γ |
|---|---|---|---|---|---|---|---|---|---|---|---|
| 05.04.93 | 7.0 | None | 7.0 | 2.0 | 0.11 | 61.2 | 42.9 | 8.5 | 10.9 | 15.8 | 21.5 |
| 17.05.93 | 9.36 | — | 9.36 | 7.0 | 0.11 | 61.2 | 45.0 | 6.5 | 7.8 | 15.7 | 25.0 |
| 02.06.93 | 4.68 | — | 4.68 | 4.0 | 0.15 | 66.9 | 41.1 | 6.4 | 7.4 | 17.7 | 27.4 |
| 28.06.93 | | | | | | 75.2 | 48.4 | 3.8 | 6.3 | 13.8 | 27.7 |

TABLE 39

Dynamics of analyses of the urine in male patient V.

| Date | Color | Reaction | Density | Trans-parency | Protein | Sugar | Leuko-cytes | Erythro-cytes |
|---|---|---|---|---|---|---|---|---|
| 24.02.93 | Yellow | Acidic | — | Transparent | — | — | 7–8 | 0–1 |
| 15.03.93 | L/yellow | Acidic | 1010 | Transparent | — | — | 1–3 | 0–1 |
| 26.04.93 | Yellow | Acidic | — | Transparent | 0.132 | — | 3–5 | 0–1 |
| 11.05.93 | Yellow | Acidic | 1011 | Transparent | — | — | 2–3 | 0–1 |
| 24.05.93 | Yellow | Acidic | 1012 | Transparent | — | — | 1–2 | single |
| 23.06.93 | Yellow | Acidic | 1011 | Transparent | — | — | 1–3 | 0–1 |
| 14.07.93 | Yellow | Acidic | 1009 | Transparent | Traces | — | 1–2 | 0–1 |

TABLE 40

Immunofermental diagnostics in male patient V.

| Date | Ag p24 | Titer AT to p24 | AT env | AT cor | Titer of total AT to HIV | Titer AT to CMV | AT IgG to HSV | AT IgM to HSV | AT IgG to EBV | AT IgM to EBV |
|---|---|---|---|---|---|---|---|---|---|---|
| 15.03.93 | neg. | 1:20.4 | + | + | 1:32000 | neg. | + | − | + | − |
| 28.06.93 | neg. | 1:12.4 | + | + | 1:32000 | not studied | + | − | + | − |
| 17.06.93 | neg. | 1:10.8 | ++ | ++ | 1:16000 | not studied | + | − | + | − |

TABLE 41

Immunoblotting in male patient V.

| Date | gp 160 | gp 120 | p 65 | p 55 | p 51 | gp 41 | p 31 | p 24 | p 18 |
|---|---|---|---|---|---|---|---|---|---|
| 16.03.92 | + | + | + | − | + | + | + | + | − |

What is claimed is:

1. A method of treating a patient having acquired immune deficiency syndrome caused by HIV-infection, comprising the steps of: preparing a medicinal preparation comprising a cell suspension from a human embryo and selected from the group consisting of human hematopoietic liver cells, human hematopoietic spleen cells, and a mixture of human hematopoietic liver cells and spleen cells and in which:

a) the contents of nucleated cells is 5 to $200 \times 10^6$;
   b) the contents of colony-forming units of granulocyte/macrophage is 20 to $200 \times 10^3$/ml;
   c) the contents of colony-forming units of granulocyte, erythrocyte, monocyte/macrophage, megakaryocyte is 0.5 to $10 \cdot 10^3$/ml, and
   d) the contents of CD34+ progenitor cells is 1 to $20 \times 10^6$/ml, and administering initially to said patient said medicinal preparation at least in one dosage, whereby an improvement in the functional activity of the immune system is provided, said improvement comprises an increase in the contents of the total amount of lymphocytes, including subpopulations of CD3, CD4 and CD8, restoration of blood indices, characterized by the normalization of the amounts of erythrocytes, leukocytes and thrombocytes; and a long-lasting decrease infectious complications and manifestations of polyneuropathy resulting in an improvement in the clinical state of the patient.

2. The method of treatment of claim 1, wherein said dosage is 0.5 ml to 5 ml.

3. A method of treatment of claim 1, in which said administration is made prior to or after a therapy carried out with the use of an etiotropic preparation.

4. A method of treating a patient having acquired immune-deficiency syndrome, caused by HIV-infection, comprising the steps of:

thawing a cryopreserved cell suspension from a human embryo and selected from the group consisting of human hematopoietic liver cells, human hematopoietic spleen cells, and a mixture of human hematopoietic liver cells and spleen cells which is stored at least in one container of a cryopreserved sample;

preparing a medicinal preparation comprising the cell suspension of the hematopoietic liver or spleen cells, or mixtures thereof, of a human embryo, and in which:

a) the contents of nucleated cells is 5 to $200 \times 10^6$/ml;
   b) the contents of colony-forming units of granulocyte/macrophage is 20 to $200 \times 10^3$/ml;
   c) the contents of colony-forming units of granulocyte, erythrocyte, monocyte/macrophage, megakaryocyte is 0.5 to $10 \times 10^3$/ml, and
   d) the contents of CD34+ progenitor cells is 1 to $20 \times 10^6$/ml; and administering initially to said patient said medicinal preparation at least in one dosage, whereby an improvement in the functional activity of the immune system is provided, said improvement comprises an increase in the contents of the total amount of lymphocytes, including subpopulations of CD3, CD4 and CD8, restoration of blood indices, characterized by the normalization of the amounts of erythrocytes, leukocytes and thrombocytes, and a long-lasting decrease in infectious complications and manifestations of polyneuropathy resulting in an improvement in the clinical state of the patient.

5. The method of treatment of claim 4, wherein said dosage is 0.5 to 5 ml.

6. The method of treatment of claim 4, wherein said administration is made prior to or after a therapy carried out with the use of an etiotropic preparation.

7. The method of treatment of claim 4, wherein in one or more subsequent administrations of the medicinal preparation, use is made of the remaining portion of the cell suspension prepared from the same embryo and stored in a bank of cryopreserved samples.

8. The method of treatment of claim 5, wherein in one or more subsequent administrations of the medicinal preparation, use is made of the remaining portion of the cell suspension prepared from the same embryo and stored in a bank of cryopreserved samples.

9. The method of treatment of claim 6, wherein in one or more subsequent administrations of the medicinal preparation, use is made of the remaining portion of the cell suspension prepared from the same embryo and stored in a bank of cryopreserved samples.

* * * * *